United States Patent [19]

Wells

[11] Patent Number: 4,994,266

[45] Date of Patent: Feb. 19, 1991

[54] PERFUMERY COMPOSITIONS

[75] Inventor: Brian L. Wells, Essex, England

[73] Assignee: Bush Boake Allen Limited, London, England

[21] Appl. No.: 376,825

[22] Filed: Jul. 7, 1989

[30] Foreign Application Priority Data

Jul. 7, 1988 [GB] United Kingdom ............. 8816209.4

[51] Int. Cl.$^5$ ............................................. A61L 11/00
[52] U.S. Cl. ..................................... 424/76.7; 239/53; 252/174.11
[58] Field of Search .................. 424/76.7; 252/174.11; 239/53

[56] References Cited

U.S. PATENT DOCUMENTS

| 3,860,525 | 1/1975 | Bechtold | 252/174.11 |
| 3,947,574 | 3/1976 | Jaggers et al. | 424/76.7 |
| 4,107,312 | 8/1978 | Wegner et al. | 424/76.7 |
| 4,454,987 | 6/1984 | Mitchell | 239/53 |

Primary Examiner—Thurman K. Page
Assistant Examiner—P. L. Prater
Attorney, Agent, or Firm—Edward J. Sites

[57] ABSTRACT

A toilet rinse block is free of para-dichlorobenzene and includes a fragrance alcohol in the form of a metal complex (e.g., citronellol aluminate) that releases the fragrance upon rinsing with water.

6 Claims, No Drawings

PERFUMERY COMPOSITIONS

This invention relates to toilet rinse blocks. These are blocks that are positioned in a toilet bowl or urinal in such a manner that they are rinsed with water when the toilet is flushed with water.

Many perfumed solid products are known and may contain perfumery compounds or complexes from which they may be obtained. Metal complexes of volatile perfumery components release the volatile fragrance on hydrolysis for example in such items as baths salts and soaps, intended for use in hot or warm water, as illustrated in GB1365063, where oligomeric titanate or zirconate esters of perfumery alcohols or phenols are used. U.S. Pat. No. 4454987 also discloses a method and apparatus for dispensing fragrances. An aluminate of a fragrant alcohol is impregnated into a carrier member such as paper or textile wick materials. On exposure to moisture in the form of water vapour, the fragrance is released.

However, these items are not used commercially and this may be due to a high water content in the product resulting in hydrolysis during storage which releases the perfumery components so that on unsealing the packaging all of the fragrance is rapidly lost. For highly porous materials, such as those described in U.S. Pat. No. 4454987, water vapour contacting the product may rapidly permeate through the whole article, releasing the perfumery component and again resulting in a very short-lived product.

Toilet rinse blocks are well known and most existing blocks have incorporated para-dichlorobenzene (PDCB) for many years either as a fragrance base, or in addition to other fragrances where it is an efficient fragrance boost, promoting longer life deodourising properties.

However, more recently, allegations of environmental toxicity problems have made PDCB an undesirable ingredient in such toilet block compositions.

No efficient alternatives have been found and at present the only alternative is to omit PDCB and use higher concentrations of more expensive fragrances, as for example, in EP0167210. However, this alternative is not wholly satisfactory because the product is more expensive and because the high concentration of the volatile perfumery component results in the product giving an initially very high odour level but the perfume rapidly evaporates and so the product has an undesirably short life-time.

It would therefore be desirable to provide a composition for toilet rinse blocks which overcomes the need for PDCB, retains long life, and avoids the need to add more concentrated and more expensive perfumes.

According to the present invention a toilet rinse block is made that is substantially free of water and para-dichlorobenzene and that is characterised in that it comprises a fragrance alcohol in the form of a metal complex from which the fragrance alcohol is released upon contact of the block with water.

The invention also includes the use of such blocks as toilet rinse blocks and methods of perfuming and cleansing a toilet by positioning a block in the toilet in a position such that it contacted by water upon flushing the toilet.

Suitable metal complexes may be titanates, zirconates or aluminates, but are preferably aluminates.

Suitable fragrance alcohols are either aliphatic or aromatic, for example, menthol, citronellol, phenyl ethyl alcohol, terpene alcohols and other volatile fragrant aliphatic alcohols or phenols.

General methods of preparation of aluminate complexes of alcohols are described in U.S. Pat. No. 2961452 and 3475476.

The alcohol derivatives are usually present in the toilet block composition in a matrix provided by other ingredients that are slowly washed away during repeated flushing. The concentration of the alcohol derivatives is usually at least 0.1% and often at least 1%. It may be up to 10% or even 15% preferably 1 to 8%. This quantity may comprise either one, or a mixture of more than one alcohol metal complex. However, some derivatives should be present at lower concentrations, for example menthol derivatives have strong fragrant properties and are preferably present at a concentration of less than 4%. In a preferred composition, other perfumery components are present in addition to the metal complexes.

The amount of free water (i.e., available for reaction) must be such that substantially no hydrolysis occurs during storage, and is below 5%, preferably below 1% and most preferably the composition contains no free water.

Since the object of the invention is to avoid the problems caused by PDCB, the toilet block composition also preferably contains no PDCB although minor amounts, e.g., below 5%, may be tolerable.

The main other constituents in the toilet blocks according to the present invention are usually selected from anionic and/or non-ionic surfactants, filler materials (usually comprising electrolytes), and optionally non-ionic polymeric materials that are not surfactants, and optionally other perfumery components.

The total amount of anionic and/or non-ionic surfactant is usually from 2 to 95%, preferably 10 to 65%. Suitable materials are for example, alkali metal salts of alkyl substituted benzene sulphonates, long chain alkyl or alkyl ether sulphates, alkane or olefin sulphonates, ethoxylated long chain fatty alcohols, alkyl ethanolamides and sulpho-succinates. Sodium dodecyl benzene sulphonate is particularly preferred.

The filler material is usually present at a concentration of from 5 to 45%. Suitable filler materials are soluble and/or insoluble materials that are not surfactants or fragrances or binders. Preferred fillers are electrolytes such as alkali metal sulphates, carbonates or phosphates. In addition, silica, calcite and clays may also be used. A particularly preferred filling agent is anhydrous sodium sulphate A polymeric binder may be included to hold the varous ingredient as a block-shaped matrix. It should not be a surfactant and should be substantially insoluble since an additional function of it preferably is that it reduces the solubility of the surfactants from the composition. Suitable polymers are usually non-ionic polymeric materials, for example polyethylene glycol, polyethylene wax and tallow alcohol. Suitable amounts are 0 to 30%, usually 2 to 10%.

In addition, minor ingredients such as dyes, bleaches, and germicides may be present.

The various ingredients will be selected from an appropriate blend of water-soluble and water insoluble components so as to ensure that a controlled small amount of the solid is dissolved away at each flush, with the result that the metal complex content is exposed gradually to water so that the block retains a long life fragrance. Preferably at least 2%, but usually below 30% and generally below 20%, of the block is formed of water insoluble material such as particulate filler and insoluble polymer.

It can be desirable to maintain a high ratio of surfactant to filler in order to achieve a stable foam.

The rinse blocks are generally formed of particulate and/or fusible ingredients that can be moulded into a block that is normally free of fibrous materials.

The composition can be mixed dry and extruded warm, e.g., at around 60 ° C. or can be melt cast. Melt casting involves mixing the components in the melt form and then casting into a tablet. However, although this is a more economical method, some perfume may be lost due to the conditions of high temperature involved in the process.

The resultant block is a slow release, long life block and the fragrant alcohol is released gradually from the metal alcohol complex by hydrolysis when the block is contacted with water as the toilet is flushed.

The block may be of any shape and size suitable for resting in or on rim holders of toilets or in urinals.

A sample of the toilet blocks according to the invention was made by melt mixing and melt casting the following components:

|  | w/w % |
| --- | --- |
| Silica | 4.6% |
| Polyethylene Wax | 6.5% |
| Sodium dodecyl benzene sulphonate | 61.9% |
| Anhydrous Sodium Sulphate | 12.0% |
| Citronellol Aluminate | 5.0% |
| Other Frangrances | 10.0% |

The resultant rim blocks were assessed for odour strength and longevity by exposing to an electronically controlled, intermittent water supply and were found to have long-life deodorising effects and good odour strength.

Comparison with proprietary products based on PDCB showed the blocks of the invention to have a satisfactory rate of solubility even though they have the advantage of not including PDCB.

I claim:
1. A solid toilet rinse block, which comprises:
   from 0.1 to 15 percent by weight of a fragrance alcohol in the form of a metal complex from which the fragrance alcohol is released upon contact of the complex with water;
   from 10 to 65 percent by weight of a surfactant selected from the group consisting of anionic surfactants, non-ionic surfactants and mixtures thereof;
   from 2 to 10 percent by weight of a substantially water-insoluble polymeric binder; and
   5 to 45 percent by weight of a filler selected from the group consisting of water soluble and water-insoluble materials;
   said block being substantially free of water and containing at least 2 percent by weight but below 30 percent by weight of water insoluble ingredients;
   whereby when the block is positioned in the bowl of a water-flushing toilet, controlled small amounts of the solid block are dissolved away at each flush, with the result that the metal complex content of the block is exposed gradually to water.
2. A block according to claim 1 comprising 0.1 to 15% by weight of the metal complex with 99.9 to 85% by weight other ingredients selected from anionic surfactants, non-ionic surfactants, fillers, non-ionic polymers, and other fragrances.
3. A block according to claim 1 in which the metal complex is selected from titanates, zirconates and aluminates of fragrance alcohols.
4. A block according to claim 1 in which the metal complex is an aluminate.
5. A block according to claim 1 in which the fragrance alcohol is selected from terpene alcohols, menthol, citronellol and phenyl ethyl alcohol.
6. A block according to claim 1 containing 1 to 8% citronellol aluminate.

* * * * *